United States Patent [19]

Dubroff

[11] Patent Number: 5,013,295
[45] Date of Patent: May 7, 1991

[54] SYRINGE FOR USE IN CATARACT SURGERY

[76] Inventor: Seymour Dubroff, 3806 Thornapple St., Chevy Chase, Md. 20815

[21] Appl. No.: 320,541

[22] Filed: Feb. 22, 1989

Related U.S. Application Data

[62] Division of Ser. No. 173,625, Mar. 25, 1988, Pat. No. 4,909,784.

[51] Int. Cl.$^5$ .............................................. A61M 1/00
[52] U.S. Cl. .......................................................... 604/38
[58] Field of Search ................... 604/22, 27, 28, 30, 604/31, 35, 36, 38, 48, 39-43, 45

[56] References Cited

U.S. PATENT DOCUMENTS

| | | | |
|---|---|---|---|
| 443,083 | 12/1890 | Bartsch | 604/38 |
| 750,276 | 1/1904 | Gruss | 604/39 |
| 1,231,772 | 7/1917 | Meyer | 604/38 |
| 4,518,383 | 5/1985 | Evans | 604/164 |
| 4,609,368 | 9/1986 | Dotson, Jr. | 128/305 |
| 4,764,165 | 8/1988 | Reimels et al. | 604/22 |

Primary Examiner—David J. Isabella
Attorney, Agent, or Firm—Epstein, Edell & Retzer

[57] ABSTRACT

A syringe, particularly useful for surgery of the eye, includes first and second tubular members disposed in concentric relation, a chamber having a piston movable therein to define a first chamber portion on one side of the piston communicating with a proximal end of the first tubular member and a second chamber portion on the opposite side of the piston communicating with a proximal end of the second tubular member such that movement of the piston forces fluid, such as a cell-killing substance, from the first chamber portion through the first tubular member and simultaneously creates a suction at the distal end of the second tubular member, for example, evacuate any substance escaping from tissue into which the substance is injected.

13 Claims, 1 Drawing Sheet

SYRINGE FOR USE IN CATARACT SURGERY

This is a divisional application of application Ser. No. 07/173,625 filed Mar. 25, 1988, now U.S. Pat. No. 4,909,784.

BACKGROUND OF THE INVENTION

1. Field of the Invention

The present invention pertains to cataract surgery and, more particularly, to the prevention of clouding of the posterior capsule after extracapsular cataract extraction.

2. Discussion of the Prior Art

Clouding of the posterior capsule after extracapsular cataract extraction, with or without the implant of an intraocular lens, has been a principal, later occurring, complication of such extracapsular cataract surgery. During cataract surgery, it is preferable to extract the natural lens while leaving the posterior portion of the lens capsule intact in the posterior chamber of the eye to provide a barrier to prevent movement or loss of the vitreous which fills the posterior chamber. If the natural lens is removed intact with the capsule, referred to as intracapsular cataract extraction, the vitreous can move through the pupil causing vitreous loss and increasing the chances of complications, such as glaucoma, corneal opacity, displacement of an intraocular lens, retinal hemorrhage, holes, breaks and detachment, and cystoid macula edema.

In many cases after extracapsular cataract extraction, with or without the implant of an intraocular lens, the posterior capsule becomes opacified or clouded due to migration of crystalline, epithelial cells into the optical zone which, clustered, form Elschnig's pearls. Along with Elschnig's pearls, visual acuity is also reduced by invading fibroblasts through metaplasia developing into myoepithelial fibers, lens fibers, collagen, fibrosis, and Sommering rings. This opacification or clouding of the posterior capsule, referred to as secondary cataract, occurs in a large percentage of extracapsular cataract extractions and is a primary cause of post operative complications.

One procedure to remove secondary cataracts is descission using a needle or scissors to punch or cut a hole in the posterior capsule. Another procedure includes the use of a YAG laser focused through the pupil to open the posterior capsule. Such procedures, referred to as posterior capsulotomy, remove the opacification to improve sight; however, they also create the adverse effects discussed above with respect to intracapsular cataract extraction due to the removal of the barrier to vitreous movement.

Other attempts to prevent clouding of the posterior capsule include constructing intraocular lenses to produce barriers to movement of the epithial cells from the equator of the posterior capsule toward the optical zone; however, such intraocular lenses have been difficult to implant in the posterior capsule and have not created effective barriers to prevent clouding.

Accordingly, there is a great need for a manner in which to prevent opacification of the posterior capsule, particularly in view of the great number of cataract surgeries performed each year and the substantial likelihood of most individuals having cataract surgery due to the natural forming of cataracts in the natural lens with aging. As noted above, the preferable procedure for cataract surgery is extracapsular cataract extraction; and, thus, much effort has been directed toward overcoming the late capsule clouding complication associated with such cataract surgery.

SUMMARY OF THE INVENTION

Accordingly, it is a primary object of the present invention to prevent clouding of the posterior capsule after extracapsular cataract extraction without requiring removal, puncturing or decission of the posterior capsule.

A further object of the present invention is to prevent clouding of the posterior capsule after extracapsular cataract extraction by killing remaining epithelial cells by osmotic cellular destruction in a hypotonic environment.

Another object of the present invention is to provide a method of performing cataract surgery on a eye to prevent capsule clouding after the surgery by injecting an cell-killing substance between the capsule and the natural lens and thereafter removing the natural lens from the eye.

The present invention has another object in that water having a salinity of less than 0.9% is injected between the capsule and the natural lens of an eye prior to removal of the natural lens to kill the epithelial cells by osmotic pressure.

Yet an additional object of the present invention is to place a viscoelastic material in the anterior chamber of an eye prior to injecting a cell-killing substance between the capsule and the natural lens such that the viscoelastic material prevents any cell-killing substance escaping from the capsule from reaching the corneal endothelium.

A further object of the present invention is to provide a syringe for injecting a cell-killing substance between the capsule and the natural lens of an eye and for aspirating any of the substance escaping from the capsule, the syringe having an aspirating tube disposed concentrically around a hollow needle with a distal end positioned adjacent the capsule to evacuate any cell-killing substance escaping from the capsule as the cell-killing substance is forced between the capsule and the natural lens by the syringe.

The present invention is generally characterized in a method of performing cataract surgery on an eye to prevent capsule clouding after the surgery comprising the steps of injecting a substance between the capsule and the natural lens, the substance having properties to kill epithelial cells, and removing the natural lens from the eye.

The present invention is further generally characterized in a syringe for injecting a cell-killing substance between the capsule and the natural lens of an eye and for aspirating any of the cell-killing substance escaping from the capsule including a hollow needle having a sharp distal end for puncturing the capsule and positioning between the capsule and the natural lens at an angle substantially tangential to the natural lens and a proximal end, an injection chamber communicating with the proximal end of the needle adapted to be filled with the cell-killing substance, an aspirating tube disposed concentrically around the needle having an open distal end proximally spaced from the distal end of the needle for positioning adjacent the capsule when the distal end of the needle has punctured and passed through the capsule and a proximal end, a piston movable in the injection chamber to force the cell-killing substance between the capsule and the natural lens, and evacuating means communicating with the proximal end of the aspirating tube for evacuating any of the cell-killing substance escaping from the capsule.

Some of the advantages of the present invention over prior art methods of preventing or eliminating capsule clouding are that the method of the present invention can be utilized along with the procedures of normal cataract surgery requiring only a single additional procedure, no difficult or complex surgical procedures are required, safety is assured by the use of viscoelastic materials and a syringe for aspirating any cell-killing substance that might escape from the capsule, and the method and syringe therefor can be inexpensively implemented.

Other objects and advantages of the present invention will become apparent from the following description of the preferred embodiment taken in conjunction with the accompanying drawings.

DESCRIPTION OF THE PREFERRED EMBODIMENT

Figure 1:
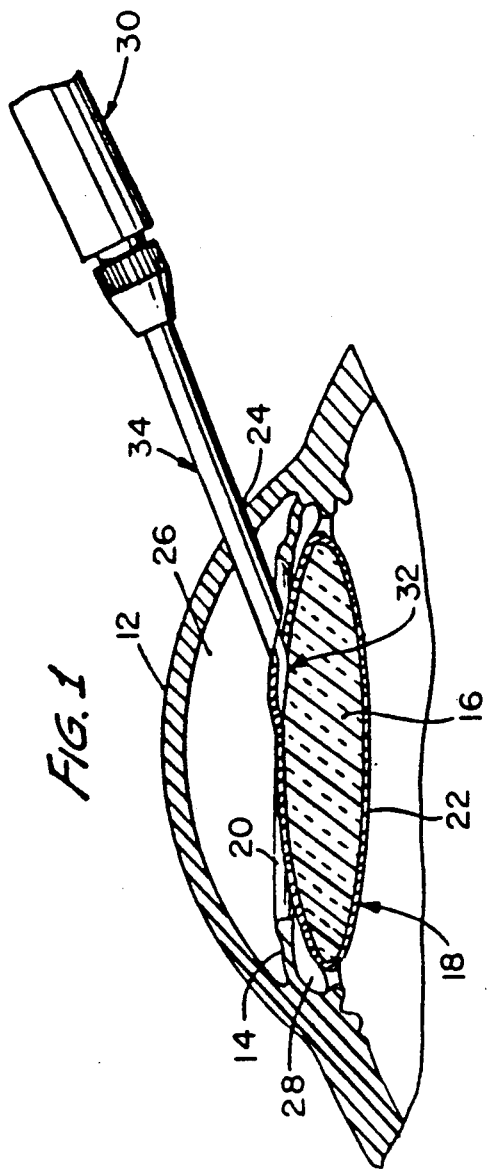
FIG. 1 is a cross-section of an eye illustrating the method of the present invention.

The method of the present invention will be explained with respect to FIG. 1 which illustrates an eye including a cornea 12, an iris 14, a natural lens 16 and a capsule 18 surrounding the lens formed of an anterior capsule segment 20 and a posterior capsule segment 22. In conventional extracapsular cataract surgery, an incision 24 is made in the cornea and an anterior capsulotomy is performed to remove a portion of the anterior segment 20 of the capsule. Thereafter, the natural lens 16 is removed; and, if desired, an intraocular lens can be positioned in either the anterior chamber 26, defined as the region between the cornea and the iris, or the posterior chamber 28, defined as the region behind the iris, posterior chamber intraocular lenses being positioned normally in the posterior capsule 22 or in the sulcus.

In accordance with the present invention, after the incision 24 is made, a syringe 30 is inserted therethrough having a hollow hypodermic needle 32. The surgeon punctures the anterior segment 20 of the capsule with the needle 32 which has an angular orientation to extend tangentially along the lens 16; and, once the needle 32 is so positioned, the syringe is operated to force a cell-killing substance between the capsule 18 and the lens 16, the substance completely surrounding the lens and killing all epithelial cells therein. The syringe 30 includes an aspirating tube 34 having an open distal end disposed adjacent the capsule to evacuate any cell-killing substance escaping from the capsule; and, further to ensure that the cell-killing substance does not come into contact with the cornea or other eye tissues, the anterior chamber 26 is filled with a viscoelastic material, such as VISCOAT produced by Cilco.

A preferred cell-killing substance is water having a salinity less than 0.9% in that the epithelial cells will be destroyed by the water in approximately thirty seconds through osmotic pressure, the cells essentially exploding. Preferably the water injected as a cell-killing substance has a salinity of from 0 to 0.6%, it being found that salinity percentages of from 0 to 0.3 are highly effective.

Figure 2:
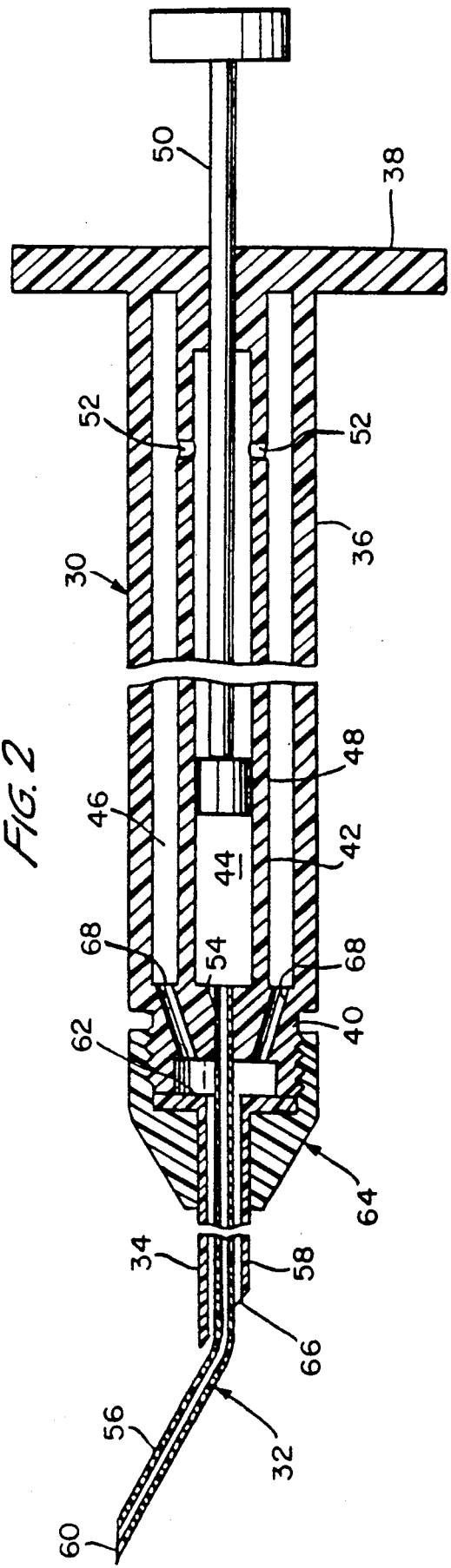
FIG. 2 is a broken cross-section of a syringe according to the present invention.

The syringe 30 illustrated in FIG. 2 represents a particularly simple and effective manner of both injecting the cell-killing substance between the capsule and the lens and aspirating any of the cell-killing substance escaping from the capsule. The syringe 30 includes a cylindrical body 36 having an end wall 38 also serving as a finger grip at its proximal end and a threaded block 40 at its distal end. A cylindrical inner wall 42 concentric with outer wall 36 extends between block 40 and end wall 38 to define an inner injection chamber 44 concentrically surrounded by an outer evacuating chamber 46. A piston 48 is movably disposed in injection chamber 44 and operable by a plunger 50 extending through end wall 38, the piston defining an injection portion of chamber 44 in front thereof and a suction portion in back thereof. The suction portion communicates with evacuating chamber 46 through passages 52 in inner cylindrical wall 42. Hypodermic needle 32 has a proximal end 54 secured in threaded block 40 in communication with chamber 44 and a distal portion 56 extending from a shank portion 58 at an angle of from 20° to 40°, the distal portion 56 terminating at a sharp distal end 60. Aspirating tube 34 has a flanged proximal end 62 clamped against threaded block 40 by a threaded coupling 64 and a beveled distal end 66 disposed adjacent the junction of the distal and shank portions of the needle 32. The aspirating tube 34 communicates with evacuating chamber 46 via passages 68 in threaded block 40.

In use, the sharp distal end 60 of the needle 32 punctures the capsule and is positioned substantially tangential to the natural lens 16 causing the open beveled distal end 66 of the aspirating tube 34 to be disposed adjacent the capsule at the puncture point. The injection portion of chamber 44 is filled with the cell-killing substance, preferably water having a salinity less than 0.9%; and, as the piston is forced into chamber 44 by depressing plunger 50, the cell-killing substance is forced through needle 32 and out distal end 60 between the capsule and the natural lens to surround the lens and kill epithelial cells therein by osmotic pressure. Any cell-killing substance inadvertently escaping from the capsule through the puncture will be collected by aspirating tube 34 since open end 66 thereof is disposed adjacent the puncture point and is subjected to suction created by movement of piston 48 via passages 52 and evacuating chamber 46. Accordingly, the cell-killing substance is prevented from contact with any eye tissue. Additionally by filling interior chamber 26 with viscoelastic material, any cell-killing substance escaping from the capsule is constrained to move along the syringe and through incision 24.

In view of the above, it will be appreciated that the method of preventing capsule clouding according to the present invention is extremely simple and efficacious in that the capsule is used to confine the cell-killing substance but is not a living cell and therefore is not affected by the cell-killing substance.

Inasmuch as the present invention is subject to many variations and modifications in detail, it is intended that all subject matter discussed above or shown in the accompanying drawings be interpreted as illustrative and not in a limiting sense.

What is claimed is:

1. A syringe for injecting a substance between the capsule and the natural lens of an eye and for aspirating any of the substance escaping from the capsule comprising hollow needle means having a distal end for penetrating the capsule and positioning between the capsule and the natural lens at an angle substantially tengential to the natural lens and a proximal end;

an injection chamber communicating with said proximal end of said needle means adapted to be filled with a substance;

an aspirating tube disposed concentrically around said needle means having an open distal end proximally spaced from said distal end of said needle means for positioning adjacent the capsule when said distal end of said needle means has passed through the capsule and a proximal end;

piston means movable in said injection chamber and adapted to force the substance between the capsule and the natural lens; and evacuating means communicating with said proximal end of said aspirating tube for evacuating any of the substance escaping from the capsule.

2. A syringe as recited in claim 11 wherein said needle means has a shank portion extending from said needle means proximal end to a first end and a distal portion extending from said first end of said shank portion at an angle of from 10° to 40° relative to said shank portion.

3. A syringe as recited in claim 2 wherein said distal end of said aspirating tube is disposed adjacent the junction of said distal and shank portions of said needle means.

4. A syringe as recited in claim 1 wherein said evacuating means includes an aspirating chamber disposed concentrically around said injection chamber.

5. A syringe for injecting a substance between the capsule and the natural lens of an eye and for aspirating any of the substance escaping from the capsule comprising a hollow needle having a sharp distal end for penetrating the capsule and positioning between the capsule and the natural lens at an angle substantially tengential to the natural lens and a proximal end;

an injection chamber communicating with said proximal end of said needle adapted to be filled with a substance;

an aspirating tube disposed concentrically around said needle having an open distal end proximally spaced from said distal end of said needle for positioning adjacent the capsule when said distal end of said needle has passed through the capsule and a proximal end;

piston means movable in said injection chamber adapted to force the substance between the capsule and the natural lens; and evacuating means communicating with said proximal end of said aspirating tube for evacuating any of the substance escaping from the capsule including an aspirating chamber disposed concentrically around said injection chamber.

wherein said piston means is disposed in said injection chamber to define an injection portion in front of said piston means and a suction portion behind said piston means, and said evacuating means includes passage means communicating with said aspirating chamber and said suction portion of said injection chamber whereby movement of said piston means forces the substance through said needle and between the capsule and the natural lens and creates a suction to evacuate any of the substance escaping from the capsule.

6. A syringe as recited in claim 1 and further comprising a cell-killing substance received in said injection chamber.

7. A medical syringe for the body comprising a syringe body;

a first tubular member having open distal and proximal ends;

a second tubular member disposed in concentric relation with said first tubular member having open distal and proximal ends; and chamber means disposed in said syringe body including piston means movable therein to define a first chamber portion on one side of said piston means communicating with said proximal end of said first tubular member and a second chamber portion on the opposite side of said piston means communicating with said proximal end of said second tubular member whereby movement of said piston means to force fluid from said first chamber portion through said first tubular member simultaneously creates a suction at said distal end of said second tubular member means to aspirate material from the body.

8. A syringe as recited in claim 7 wherein said first tubular member is a hollow needle for injecting fluid in bodily tissue, and said second tubular member is an aspirating tube.

9. A syringe as recited in claim 8 wherein said aspirating tube is disposed around said needle.

10. A syringe as recited in claim 9 and further comprising as aspirating chamber disposed concentrically around said chamber means and communicating with said second chamber portion and said proximal end of said aspirating tube.

11. A syringe as recited in claim 8 wherein said open distal end of said aspirating tube is proximally spaced from said distal end of said needle.

12. A syringe as recited in claim 11 wherein said aspirating tube is disposed around said needle and said needle is formed of a shank portion extending from said proximal end of said needle and a distal portion extending from said shank portion to said distal end of said needle, said shank portion being axially aligned with said chamber means and said distal portion extending from said shank portion at an angle of from 10° to 40° relative to said shank portion.

13. A syringe as recited in claim 12 wherein said distal end of said aspirating tube is disposed adjacent the junction of said distal and shank portions of said needle.

* * * * *